United States Patent [19]

DeHaan et al.

[11] Patent Number: 5,068,883
[45] Date of Patent: Nov. 26, 1991

[54] HAND-HELD CONTRABAND DETECTOR

[75] Inventors: Daniel DeHaan, San Diego; David L. deLesdernier, Encinitas, both of Calif.

[73] Assignee: Science Applications International Corporation, San Diego, Calif.

[21] Appl. No.: 522,274

[22] Filed: May 11, 1990

[51] Int. Cl.$^5$ ............... G01N 23/203; G21F 5/012
[52] U.S. Cl. ........................... 378/86; 378/88; 378/83; 378/197; 250/498.1
[58] Field of Search ............... 378/88, 198, 197, 86, 378/87, 83; 250/496.1, 497.1, 498.1

[56] References Cited

U.S. PATENT DOCUMENTS 4,494,001 1/1985 Peck .................... 250/358.1

Primary Examiner—Edward P. Westin
Assistant Examiner—Don Wong
Attorney, Agent, or Firm—Fitch, Even, Tabin & Flannery

[57] ABSTRACT

A light-weight hand-held contraband detection system (10) includes two different sources (74) of low energy gamma rays. Each gamma ray source selectively emits gamma rays at a different energy level, which gamma rays are directed to a specific volume (30) of an object, e.g. a vehicle, being searched. The hand-held detection system also includes a gamma ray detector (42) coupled to a visual indicator (14), which indicator visually indicates the relative number of back-scattered gamma rays reflected back from the object being searched. Back scattering of the emitted gamma rays occurs in differing degrees depending upon the density and contents of the particular volume of the object receiving the gamma rays. Certain changes in density reflect the possibility that contraband, such as drugs, may be concealed in the object being searched. In use, the system is gripped in a hand of the user and passed over the surface of the object being searched. A mechanical latch (80, 82, 90, 92, 94) allows a user to use the system without having to continually press a thumb switch (22). The indicator (14) on the device is detachable from the housing, but remains electrically connected to the housing through an umbilical cord. One embodiment of the detection system also includes audible alarm means (54, 59) for providing an audible indication to the user of the relative number of backscattered gamma rays.

10 Claims, 3 Drawing Sheets

HAND-HELD CONTRABAND DETECTOR

BACKGROUND OF THE INVENTION

The present invention relates to apparatus and devices for detecting contraband, and more particularly to a hand-held contraband detector designed to detect contraband, such as drugs, hidden behind panels or inside of an enclosure within a few inches of the hand-held device.

Law enforcement agencies, including customs officials, charged with searching persons and property for concealed contraband, face an ever increasing and more difficult challenge as increased amounts of illegal contraband are transported from one location to another, particularly where such contraband is hidden or concealed with increased ingenuity while in transit. Hence, there is an increased need for reliable, easy-to-use, contraband detectors to assist such law enforcement agencies as they perform their never-ending vigil to detect illegal drug traffic.

It is known in the art to provide a hand-held contraband detector device that includes a single source of low energy gamma rays. In use, the hand-held device is scanned over an area being searched, i.e., over a target volume (an object being investigated), so that the low energy gamma rays are directed into the target volume. Depending upon the composition of the target volume, a portion of the gamma rays are backscattered and returned to the hand-held device. By quantitatively sensing these backscattered gamma rays, a rough qualitative determination can be made as to the density composition of the target volume. From such density information, reasonable inferences may be drawn as to whether the target volume includes certain types of contraband material. If contraband is sensed, an indicator on the sensor changes sufficiently to alert the searcher that contraband may be present. In this way, the hand-held detector greatly aids the searcher in locating concealed contraband.

Despite the advantages provided to the searcher with such prior hand-held detectors, the use of such detectors has also created some problems. For example, prior detectors of this type have frequently used americium 241 as the single source of low energy gamma rays. Unfortunately, the energy of the gamma rays available from americium 241, approximately 60 KeV, is not sufficient to allow the gamma rays to readily penetrate some common materials wherein contraband may be hidden, although it is well suited for detecting contraband in other common materials. Thus, the searcher, while readily detecting contraband in some materials using such device, does not detect identical contraband in other materials. Hence, much contraband is not detected using such prior devices.

Further, many prior hand-held detectors have been housed in a pistol-shaped housing in an attempt to make such detectors easier to handle and use. Unfortunately, this configuration has proven to be somewhat threatening for most searchers and searchees as the detector has the rough appearance of a firearm that the searcher is pointing at the searchee or the searchee's property.

One type of prior hand-held detector uses barium 133 as the single source of rays. Advantageously, barium 133 provides gamma rays having more energy (approximately 350 KeV) than the gamma rays from americium 241, thus allowing the gamma rays to more readily penetrate the different types of materials in which contraband may be concealed. However, in order to properly shield the increased energy gamma ray source, such unit includes a structure that is much heavier than the device using americium 241. Further, in order to release the gamma rays from the device, the user must continually hold down a spring-loaded trigger handle. Use of this device may thus become very tiring as the user must both lift a heavier device and continually depress the spring-loaded trigger.

Another problem associated with prior hand-held contraband detectors relates to the manner in which the device signals that contraband has been detected. Prior devices typically include an indicator, either a digital or analog readout device, that provides a visual indication to the user of the amount of backscattered gamma rays received, and hence an indication of the composition of the target volume. Unfortunately, this indicator is integrally included as part of the hand-held detector. Hence, in scanning hard-to-reach locations, such as under a table or inside of the fender well of a motor vehicle, the user must frequently place himself or herself in difficult positions in order to be able to place the detector in the desired location while still being able to see the indicator on the detector.

In view of the foregoing, it is evident that what is needed is a light-weight hand-held contraband detection device that is ergonomically easily to use, is not threatening to either the searcher or the searchee, and produces reliable, consistent results regardless of the materials in which the contraband may be hidden. The present invention advantageously addresses these and other needs.

SUMMARY OF THE INVENTION

In accordance with one aspect of the present invention, a light-weight hand-held contraband detector is provided that detects contraband hidden behind panels or inside of an enclosure. The detector includes a housing having the general appearance and size of a brick. Inside of the housing are two different sources of low energy gamma rays, americium 241 and barium 133. The energy of the gamma rays emitted from each source is different, with the energy of americium 241 gamma rays being approximately 60 KeV, and the energy of the barium 133 gamma rays being approximately 350 KeV. Upon opening a shutter, gamma rays from both sources are directed to a specific target volume of an object being searched. Such object may be, e.g., a boat hull, tires, doors, fenders, bumpers, fuel tanks, aircraft structures, or building walls. The relative number of scattered gamma rays reflected back from the object varies as a function of the density and contents of the particular volume of the object receiving the gamma rays. The backscattered gamma rays are detected by a suitable gamma ray detector within the housing, which gamma ray detector is coupled to a detachable visual indicator. A significant change in the number of backscattered gamma rays detected thus signals the possibility that contraband, such as drugs, may be concealed in the object being searched. In one embodiment of the invention, an internal audible alarm is also sounded to audibly indicate the likely presence of contraband. In use, the device emits short beeps, at a rate roughly proportional to the change in target density.

In use, the detector of the present invention is conveniently gripped in a hand of the user (searcher) and simply passed over, or otherwise positioned near, the surface of the object being searched. A mechanical latch advantageously allows the user to open the shutter of the device without having to continually press a thumb switch. Advantageously, the indicator on the device is detachable from the housing, remaining electrically connected thereto through an umbilical cord, thereby allowing the housing to be readily inserted under or into areas in which it might otherwise be difficult to see, while maintaining the indicator in an easily seen position. Advantageously, the display is backlit, allowing use in low ambient light situations.

Thus, the present invention may be broadly characterized as a system for detecting concealed contraband in an object under investigation, such system including: (a) means for selectively directing low energy gamma rays into respective small volumes of the object under investigation; (b) means for measuring the relative quantity of backscattered gamma rays from each of the small volumes; and (c) means for determining any significant change in the quantity of backscattered gamma rays measured from one small volume to an adjacent small volume, where any such significant change provides an indication that one of the volumes may contain contraband.

Further, with such system, it is noted that the present invention encompasses a method of detecting concealed contraband, this method comprising: (a) selectively directing low energy gamma rays into a first volume of an object being investigated for the presence of concealed contraband; (b) measuring the quantity of backscattered gamma rays from the first volume; (c) directing the low energy gamma rays at other volumes of the object and measuring the relative quantity of backscattered gamma rays from each of the other volumes; and (d) using any significant change in the quantity of backscattered gamma rays measured from one volume to an adjacent volume as an indication that one of the volumes may contain contraband.

It is a feature of the present invention to provide a light-weight hand-held contraband detector that is ergonomically easy to use and operate.

It is another feature of the invention to provide such a contraband detector that is not shaped like or otherwise have the appearance of a gun or other threatening device, thereby allowing the detector to be freely used without creating a confrontational or threatening environment.

A still further feature of the invention provides a mechanical latch that allows the user to use the device without having to continually press a spring-loaded thumb switch. This latch is designed to automatically release if the unit is jarred, e.g., dropped, to enhance user safety.

Yet another feature of the invention provides such a detector employing a plurality of low energy gamma ray sources, each of which emits low energy gamma rays at a different energy than the other(s), thereby allowing a much wider variety of material to be checked for hidden contraband than has heretofore been possible.

A further feature of the invention provides a light-weight hand-held detector that includes means for allowing the device to be used in hard-to-see locations, such as into crevices. A detachable readout device, for example, allows the detector to be used in hard-to-see locations, while at the same time maintaining the indicator at a readily visible location apart from the hard-to-see location. An audible alarm provides a similar function.

BRIEF DESCRIPTION OF THE DRAWINGS

The above and other aspects, advantages and features of the present invention will be more apparent from the following more particular description thereof, presented in conjunction with the following drawings, wherein.

DETAILED DESCRIPTION OF THE INVENTION

The following description is of the best mode presently contemplated of practicing the invention. This description is not to be taken in a limiting sense, but is made merely for the purpose of describing the general principles of the invention. The scope of the invention should be ascertained with reference to the claims.

Figure 1:
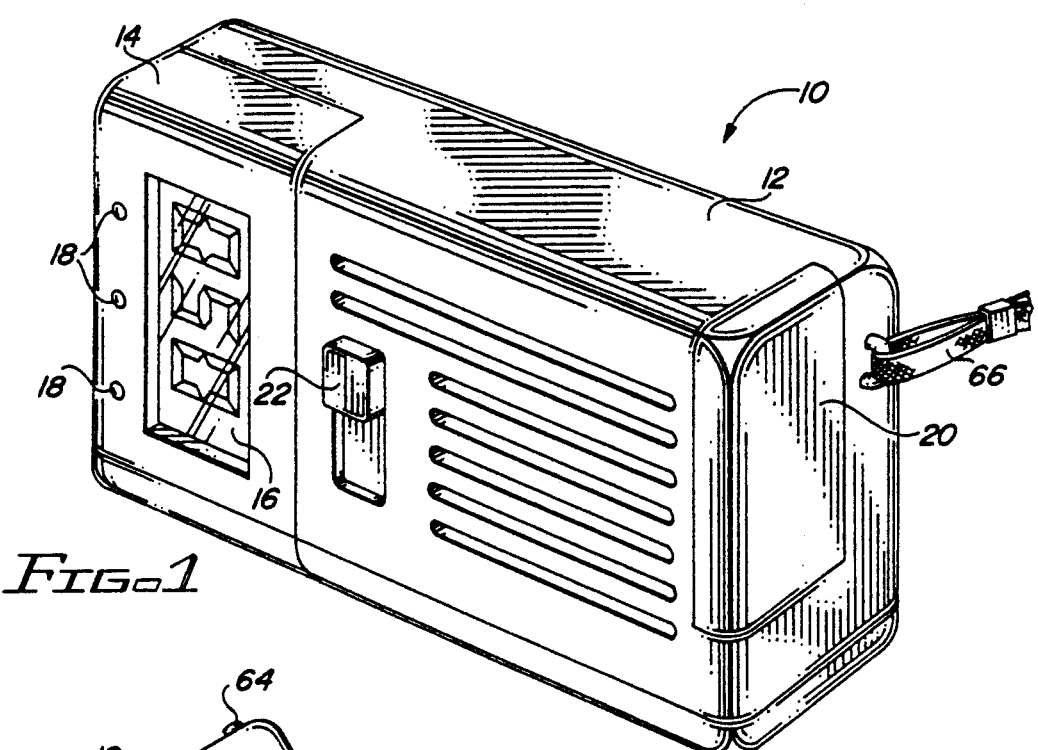
FIG. 1 is a perspective view of a hand-held contraband detector made in accordance with the present invention.

Referring first to FIG. 1, there is shown a perspective view of a hand-held contraband detector 10 made in accordance with the present invention. As seen in FIG. 1, the detector 10 includes an ergonomically designed housing 12 adapted for easily being held in a hand of a user. A visual indicator 14 is detachably secured to the housing 12. The visual indicator 14, in the preferred embodiment, includes a digital display 16, as well as a plurality of LED's (light emitting diodes) 18. A battery compartment is located behind a removable panel 20. A suitable battery pack may be removably inserted into this compartment in order to provide operating power for the detector 10. Such battery pack, in accordance with a preferred embodiment, is rechargeable.

A slidable thumb switch 22 provides a means for turning the detector 10 ON or OFF. As explained more fully below, when OFF, the detector 10 does not operate, and may be easily carried, e.g., in a holster, by its user until the user encounters an object wherein concealed contraband may be located. Upon encountering such an object, the user removes the detector from its holster and holds it adjacent to a portion of the object. The user then slides the thumb switch 22 to the ON position, and scans the object by sliding the detector over those portions of the object to be investigated.

With the detector ON, one of the LED indicators 18 is energized, and low energy gamma rays are directed from a side of the detector 10 facing the object (the backside as the device is oriented in FIG. 1) towards the object. Such gamma rays penetrate into the object.

However, depending upon the density and contents of the object, some of the gamma rays are reflected back to the detector 10. The number of low energy gamma rays that are thus reflected are referred to as backscattered gamma rays, and the relative number of such backscattered gamma rays advantageously provides an indication of the density and contents of the object. Thus, the detector 10 includes means for detecting and counting the backscattered gamma rays, with the relative number of such gamma rays being displayed on the digital display 16 and/or indicated through an audible signal (heard, e.g., through a beeper circuit).

Figure 2:
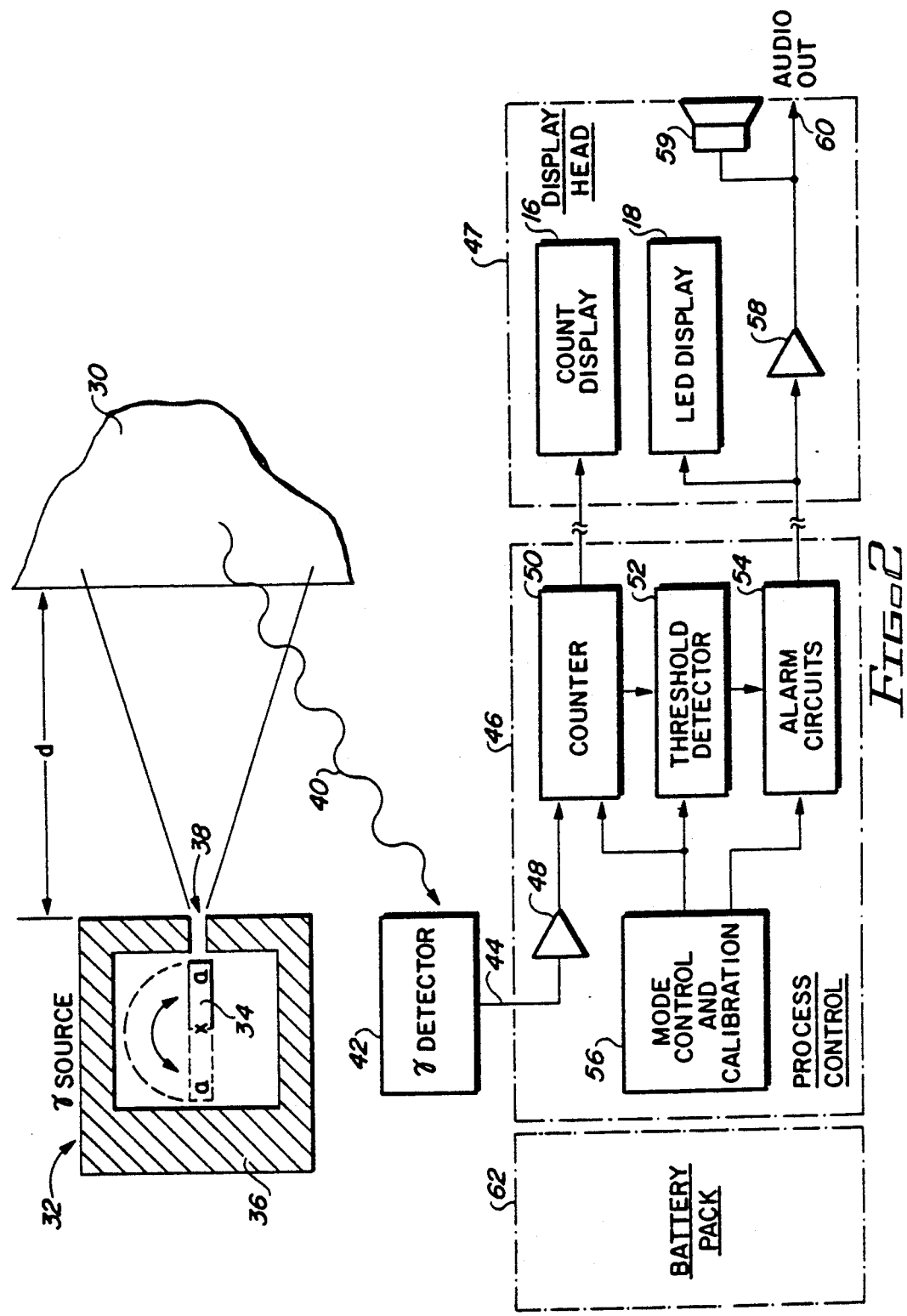
FIG. 2 is a schematic block diagram of the present invention.

Referring next to FIG. 2, there is shown a schematic block diagram of the hand-held contraband detector of the present invention. Included in FIG. 2, besides the various elements housed inside of the housing 12, is an object 30 being investigated. At the heart of the detector 10 is a gamma ray source assembly 32 ($\gamma$ source assembly). The $\gamma$ source assembly 32 includes a mechanical shutter mechanism that selectively allows gamma rays to be directed to the object as controlled by the thumb switch 22. Included within the assembly 32 is at least one source of low energy gamma rays 34. Preferably, the source of low energy gamma rays 34 emits gamma rays primarily only from one end thereof, e.g., the end marked "a" (active) in FIG. 2. A collimator opening or aperture 38 in the shielded housing 36 allows a significant number of gamma rays from the source 34 to exit therethrough only when the active end "a" of the source 34 is positioned adjacent thereto (shutter OPEN). Advantageously, the source 34 is movable within the shielded housing 36, so that the active end "a" of the source 34 may be selectively positioned away form the aperture 38 when gamma rays are not desired (shutter CLOSED).

As explained more fully below, in a preferred embodiment, a spring bias force may be used to maintain the active end "a" of the source 34 away from the aperture 38 at all times except when the detector 10 is actually being used to scan an object, at which time the operator manually moves the thumb switch 22 (FIG. 1) to move the active end "a" next to the aperture 38. A mechanical latch may be used to maintain this operating position for so long as the operator desires, thereby allowing the operator to remove his thumb from the latched switch 22 while scanning an object with the device.

The gamma rays exiting the aperture 38 are directed towards and into the portion of the object 30 fronting the aperture 30. A distance "d" separates the aperture opening from the fronting surface of the object. This distance "d" is preferably a very small distance, e.g., less than ¼ inch, thereby ensuring that the gamma rays enter the object rather than reflect from its surface.

Depending upon the contents of the object 30, particularly depending upon the density of the object 30 in the volume immediately behind its surface, differing amounts of gamma rays are backscattered to the detector. Such backscattered gamma rays are symbolically depicted in FIG. 2 as a wavy arrow 40.

The backscattered gamma rays 40 are detected by a gamma detector 42. Such gamma detector 42 may be of any suitable type, such as a scintillation detector. Detected gamma rays are manifest by a momentary "flash" or electrical pulse signal appearing on an output signal line 44. This output signal line is connected to process control circuitry 46. The process control circuity, in turn, is coupled to a display head 47.

The process control circuitry 46 includes an amplifier 48, a counter 50, a threshold detector 52, alarm circuits 54, and mode control and calibration circuitry 56, or circuitry that performs the function of such circuits. In a preferred embodiment, all such circuits, with the exception of the amplifier 48 and portions of the alarm circuits 54, may be realized using a conventional microprocessor.

The display head 47 includes the digital display 16, the LED display 18, an audio drive circuit 58, and internal speaker 59. The digital display 16 is preferably a low power Liquid Crystal Diode (LCD) Display. In some embodiments of the invention, the audio drive circuit 58 may be coupled to an audio output terminal 60, to which earphones may be detachably connected. Preferably, the drive circuit 58 drives the internal audio speaker 59, or equivalent device, so that audio beeps can be audibly discerned.

A rechargeable battery pack 62 provides the requisite electrical operating power for the detector 10.

In operation, the amplifier 48 amplifies the relatively weak signals from the gamma detector 42 so that such can be further processed. The amplifier 48 may form part of a conventional photomultiplier assembly. The counter 50 effectively counts the number of gamma rays that are detected by the gamma detector 42. The counted gamma rays are compared to preset values in the threshold detector 52, which preset values are defined by the mode control and calibration circuitry 56. In some operating modes, the preset values may be a "reference count" obtained as explained below. If the preset values are exceeded, the alarm circuits 54 are triggered. An audio beeper may form part of the alarm circuits 54. In some embodiments, this audio beeper may be disabled, so that only a person wearing earphones connected to the audio output terminal 60 is allowed to hear the audio beep generated by the alarm circuits 54. However, in a preferred embodiment, and as a safety precaution, an audible beep is generated at least every two seconds when the shutter is open to serve as a reminder that the device is ON.

Figure 3A:
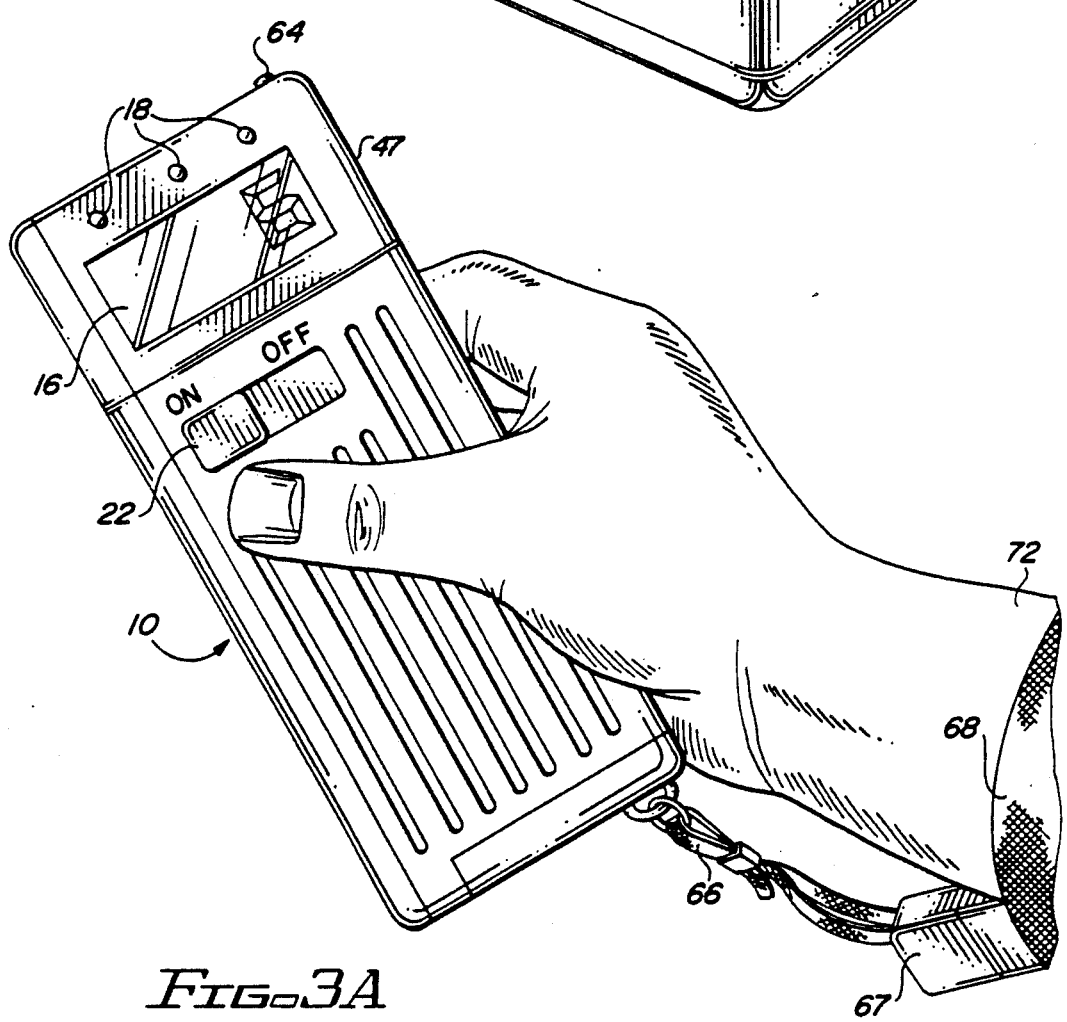
FIG. 3A shows the detector of FIG. 1 held in the hand of a user, and thus illustrates the relative size of the detector.
Figure 3B:
FIG. 3B shows a user of the detector, such as a customs official, scanning a car door with the invention to determine in contraband is hidden in the door panel.

Referring next to FIGS. 3A and 3B, there is shown the detector 10 of FIG. 1 being held in the hand of a user 72. As seen in FIG. 3A, the detector 10 is of a convenient size to be readily held by its user in one hand. Advantageously, the display head 47 may be rotated on a hinge pin 64, or equivalent, in order to facilitate its visibility. If needed, the entire display head 47 may be removed from the body of the detector 10, thereby allowing the body of the detector 10 to be inserted into crevices, e.g., within a fender well of a vehicle, while keeping the display head in a location where it is readily visible. An adjustable strap 66, secured to the body of the detector 10, may be detachably coupled by means of a locking clip 67, to a wrist strap 68 secured around a wrist of the user. As seen in FIG. 3B, the user 72 (e.g., a customs official or law enforcement personnel) may use the detector 10 to scan the door of an automobile 70 to determine whether contraband may be hidden inside the door panel.

Referring next to FIGS. 4, 5, 6A and 6B, additional details associated with the gamma ray source assembly 32 (FIG. 2) are shown. In particular, these drawings illustrate a preferred embodiment of a shutter mechanism that selectively permits gamma rays from the gamma ray source 34 to irradiate an object under investigation.

Figure 4:
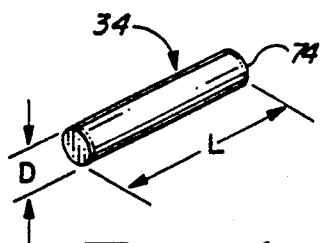
FIG. 4 depicts a gamma ray source.

FIG. 4 depicts a cylindrical housing 74 of the radioactive source 34 (FIG. 2). The preferred radioactive sources are BA-133 or AM-241. Such sources may be obtained commercially from numerous vendors, such as Amersham, of Arlington Heights, Ill. As seen in FIG. 4, the cylindrical housing 74 of the source 34 has a length L and a diameter D. For the quantity of radioactive material required for the present invention, the cylindrical housing 74 may be quite small, e.g., L=10 mm and D=2.0 mm for BA-133; L=10 mm and D=3.0 mm for AM-241. The maximum activity of the BA-133 source is on the order of 500–1000 microcurie, while for the AM-241 source it is on the order of 14 millicuries.

Figure 5:
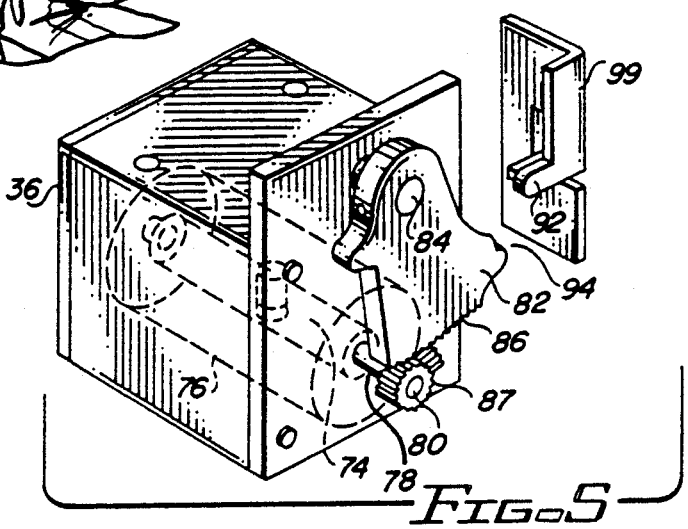
FIG. 5 diagrammatically illustrates a shutter mechanism used in the detector of FIG. 1 for holding a plurality of gamma ray sources of the type shown in FIG. 4, and allowing such sources to be selectively positioned for emission of gamma rays.
Figure 6A:
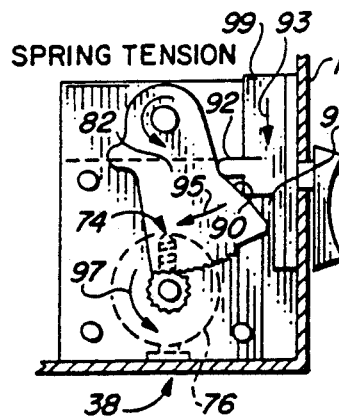
FIGS. 6A and 6B illustrate front and top views, respectively, of the shutter mechanism and shield assembly of FIG. 5.
Figure 6B:
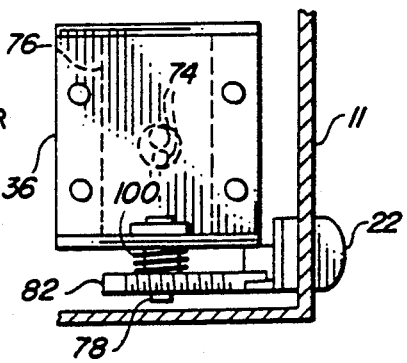

Referring next to FIGS. 5, 6A, and 6B, the cylindrical housing 74 for each different source material is radially placed in a drum 76 so that one end of the housing 74 is near a center longitudinal axis of the drum 76, and the other end is near a circumferential surface of the drum 76. The drum 76 is mounted for rotation about its longitudinal axis on a shaft 78. The shaft 78, or equivalent, passes through the shielded housing 36. At one end of the shaft 78 is a gear 80. A lever 82 is pivotally mounted above the gear 80 on a second shaft 84. One edge of the lever 82 has a series of teeth 86 therein. These teeth engage matching teeth 87 around the circumference of the gear 80. Thus, as the lever pivots on the shaft 84, the drum 76 rotates.

As seen best in FIG. 6A, the lever 82 includes a sloping edge 90 adapted to engage a protruding finger 92 from a bracket 99 attached to the backside (i.e., on the inside of a wall 11 of the detector housing 10) of the sliding thumb switch 22. As the thumb switch 22 is slid in the direction of the arrow 93, the finger 92 pushes against the sloping edge 90 of the lever 82, thereby causing the lever 82 to pivot in the direction of the arrow 95. As the lever thus pivots, it causes the drum 76 to rotate in the direction of the arrow 97. As the lever 82 continues to pivot, and as the drum 76 continues to rotate, the finger eventually reaches a point where it engages a recess 94 located at the wide end of the sloping edge 90. Once the finger 94 engages the recess 94, the lever remains latched in this position until a manual force is asserted to slide the thumb switch 22 in a direction opposite that of the arrow 93, thereby forcing the finger 92 out of recess 94.

The number of teeth 86 along the edge of the lever 82 are designed to be equal to one-half the number of teeth around the circumference of the gear 80. Hence, movement of the lever 82 through its entire stroke distance, causes the drum 76 to rotate one-half turn, or 180°. The radioactive sources 74 are mounted in the drum 76 so as to have their respective active ends the farthest possible distance from the collimator opening or aperture 38 when the shutter mechanism is OFF (i.e., with the lever 82 in its farthest most counterclockwise position as viewed in FIG. 6A); and the closest possible distance from the collimator aperture 38 when the shutter mechanism is ON (i.e., with the lever 82 in its farthest most clockwise position as viewed in FIG. 6A, and with the finger 92 engaging the recess 94). The collimator aperture or opening is 0.25 inches in diameter in the preferred embodiment.

A spring 100 (best seen in FIG. 6B), engages the lever 82 to the shielded housing 36, and asserts a bias force that tends to rotate the drum 76 in a clockwise direction (as viewed in FIG. 6A). Sliding the thumb switch 22 in the direction 93, forces the drum to rotate counterclockwise, against the spring force. Engaging the finger 92 in the recess 94 locks or latches the drum in the corresponding location, until the finger 92 is manually forced out of the recess 94 by sliding the thumb switch in the opposite direction, or until external forces, such as an impact force (caused, e.g., by dropping the unit), also releases the finger 92 from the recess 94. Thus, the spring force tends to rotate the shutter mechanism to its OFF position. However, when fully rotated to its ON position, the shutter mechanism will remain latched in such OPEN position until the thumb switch 22 is manually forced therefrom, or until an impact force creates the same effect. The radioactive sources 74 are thus surrounded with appropriate shielding in all directions, except when the shutter mechanism is rotated to its ON position.

The shielded housing 36 is preferably a lead alloy or tungsten cube measuring approximately 1.3 inches on a side. The drum 76 is suspended and retained within this housing by means of the shaft 78, as above described, and teflon bearings. The amount of shielding surrounding the sources 74 is approximately 0.5 inches of lead in all directions. This level of shielding limits the external radioactive dose rate to less than 1 mr/hr at the external surface.

For safety reasons, the detector 10 is designed to encounter difficult environments, including temperature extremes and mild shocks such as short drops. The case of the detector 10 is preferably constructed of a rugged molded plastic and a machined aluminum base. Conditions that would destroy the housing would have little effect on the shielded source housing 36. The spring 100 is captive to the shield housing, and is thus not affected by damage to the base or cover.

As further safety precautions, an OPEN or ON shutter mechanism may be ascertained in several ways, including: (a) the presence of characters on the LCD display 16; (b) the illumination of any one of the three LED's 18; (c) the physical position of the thumb switch 22; or (d) the presence of an audible beep at least every two seconds, which audible beep serves as a reminder that the shutter is open.

In operation, the radioactive sources 74 are rotated so that they may emit a narrow beam of radiation, i.e., gamma rays, out through the collimator opening 38. This beam passes into and through the object under investigation. Some of this beam is reflected back, or backscattered, to the detector 42. The amount of backscattered radiation is counted by the radiation detector 42, and associated processing circuitry. The rate of backscattered radiation is referred to as the "count rate".

The process and control circuitry 46, e.g, a microprocessor, keeps track of the count rate from the gamma detector 42 as the hand-held device 10 is moved along a surface being examined. The digital display 16 and audio beeper notify the operator as the count rate changes. Varying count rates, while scanning, indicate the presence or absence of material or structure behind the subject surface.

Heavy materials, such as steel, tend to absorb the radiation, while light organic materials, such as narcotics, alcohol, and explosives, tend to reflect the radiation. This effect is analogous to medical X-ray, where materials of different density, such as bone and tissue, appear differently to the X-rays.

The hand-held detector, in a preferred embodiment, has three modes of operation: In a first mode, or MODE 1, the unit displays the count rate, and the audio beeper is not functional. This is the default mode when the unit is first energized. This mode may be used as a calibration mode for determining a "reference count rate" for use in the other two modes.

In a second mode, or MODE 2, the unit processes the current count rate against the count rate that was measured at the time MODE 1 was excited (i.e., the "reference count rate"). The displayed value is the number of standard deviations between the current count rate and the reference count rate. This value (number of standard deviations) may be positive or negative, and its magnitude is representative of the difference in density between the area currently being scanned versus the reference area (the area from which the "reference count rate" was obtained.

While in MODE 2, if the displayed value increases (or decreases) beyond ±3, a beeper will start to sound at a rate proportional to the displayed value. This beeper makes it possible to scan a surface without watching the display. An increasing beep rate indicates the presence (or absence) of an object behind the surface which is either absorbing or reflecting the radiation.

For example, the unit 10 may be used to scan a car door, as shown in FIG. 3B. The unit may be calibrated in the center of the door, i.e., the reference count rate is obtained from the center of the door with the unit in MODE 1. The unit is then switched to MODE 2 and slowly scanned over the surface of the door. Steel structures inside the door will absorb radiation, so as the unit is passed over such a structure, the MODE 2 value may dip negative. If the unit is calibrated over such a structure, as it moves away, the MODE 2 value may increase. Such small fluctuations are normal. However, a significant change in the value is a sign of some substance, such as contraband, behind the surface moving in or out of the detector's field of view.

In a third mode, or MODE 3, the operation is the same as for MODE 2 described above, except that the displayed value is simply the difference in count rates, i.e., the current count rate minus the reference count rate. The audio beeper rate is determined that same as in MODE 2.

To use the hand-held detector 10, the base of the unit (the side having the collimator aperture 38 therein) is placed against a surface of the object to be investigated. The device is actuated by sliding the thumb switch 22 in the appropriate direction. As described above, movement of the thumb switch 22 causes the finger 92 to internally act against the spring-loaded lever/gear mechanism comprising the lever 82, gear 80, and spring 100, causing the drum or source holder 76 to rotate. This action orients the sources 74 downward toward the base of the unit, positioning them adjacent the opening 38 in the bottom of the shield assembly. When the thumb switch 22 is fully actuated, the shutter will latch open as the finger 92 engages the recess 94 of the lever 82. The shutter is closed by a light upward pull on the thumb switch 22, freeing the finger 92 from the recess 94, and allowing the spring to rotate the drum 76 to the closed position.

Rotation of the gear 80, and associated components, also actuates an internal switch that energizes the electronic circuitry. As indicated, the display head 47 swings out from the side of the unit, thereby allowing the display to be more visible. The angle of the display may be adjusted by the operator as desired to any of several detent stops. If necessary, the display head 47 can also be removed from the unit and held in hand while the source-detector unit is used to examine recessed and hidden areas.

The three LED's 18 signal the operating mode of the device. The leftmost LED, when illuminated, indicates the unit is in MODE 1. The center LED, when illuminated, indicates operation in MODE 2. The rightmost LED, when illuminated, indicates operation in MODE 3.

Three push button switches are located on the side of the device. One switch is labeled "MODE" and is used to sequentially step through the three operation modes. The switch labeled "HOLD" is used to freeze the current display value. A momentary press on this switch also causes the audio beeper to stop, and causes the current mode LED to flash. Normal operation may be resumed with another momentary press on the HOLD button. The switch labeled "LAMP" is used to toggle a backlight on the LCD display on and off. Use of the backlight operation in poor ambient light conditions allows the display to be better seen, but reduces the battery charge life.

The variable-rate audio beep function may be selectively disabled by moving the "beeper disable" switch to the OFF position. In the preferred embodiment, this switch is accessible through a hole in the side of the display head.

It is noted that when using the device, some care should be exercised to keep the base of the unit consistently flush against the surface being scanned. Otherwise, the unit will respond to radiation reflected off the surface of the object being examined rather than seeing only the radiation reflecting from behind the surface.

Advantageously, the hand-held detector 10 may be calibrated against a known calibration surface. The count rate against this surface is then compared with an expected count rate, and the ratio is used as a scaling constant for all subsequent counting. This feature advantageously assures that unit-to-unit performance is consistent.

To utilize the calibration feature, the base of the device 10 is placed against the calibration surface. All three push button switches on the side of the unit are depressed simultaneously, the shutter mechanism is OPENED (by sliding the thumb switch 22), and the switches are released. When done properly, the display shows "- - - ", and all three LED's 18 illuminate. At this point, the MODE switch is momentarily pressed, and the unit displays the unscaled raw count rate. To cancel the calibration, the thumb switch shutter lever is released, and the unit is turned OFF. To continue with the calibration, the MODE switch is again momentarily pressed, placing the device in MODE 1. All subsequent counts are then scaled using the new calibration, until the unit is recalibrated.

As described above, it is thus seen that the present invention provides a light-weight hand-held contraband detector that is ergonomically easy to use and operate. A mechanical latch, for example, allows a user to activate the device without having to continually press a spring-loaded thumb switch, as has been common with similar prior art devices. Further, the contraband detector is deliberately shaped to have the appearance of a relatively benign device, i.e., a brick, thus avoiding the appearance of a gun or other threatening instrument. These features advantageously allow the detector to be easily and freely used without causing undue fatigue on the part of its user, and without creating a potentially explosive confrontational situation between the user and a person being searched.

Further, as described above, it is seen that the detector employs a plurality of low energy gamma ray sources, each of which sources emits low energy gamma rays at a different energy than the other gamma ray sources. This feature advantageously allows a much wider variety of material to be checked for hidden contraband than has heretofore been possible.

Finally, it is seen that the detachable readout indicator and/or audible alarm features of the present detector advantageously allow the device to be easily used in hard-to-see locations, such as into crevices, wheel wells, under vehicles, and the like.

While the invention described herein has been described with reference to particular embodiments and applications thereof, numerous variations and modifications could be made thereto by those skilled in the art without departing from the spirit and scope of the invention as claimed.

What is claimed is:

1. A portable contraband detection system for detecting contraband concealed within an object, said detection system comprising:

gamma ray generating means for generating low energy gamma rays, said gamma ray generating means being located within a shielded housing having a collimator opening, said gamma ray generating means including means for generating gamma rays having a plurality of prescribed energies;

shutter means for selectively directing said low energy gamma rays through said collimator opening or into said shielded housing, said shutter means including a shutter assembly having a closed position wherein said gamma rays are absorbed into said shielded housing, and an open position wherein said gamma rays are directed through said collimator opening, said shutter assembly comprising:

a shaft passing through said shielded housing, a drum mounted for rotation about its longitudinal axis on said shaft, means for receiving a plurality of radioactive sources within said drum, each of said radioactive sources having a prescribed energy, each radioactive source being contained in a housing having an open end and a closed end, said closed end being held in said drum so as to be near the longitudinal axis of said drum, said open end being near a circumferencial surface of said drum, means for selectively rotating said drum 180°, said open position corresponding to positioning said drum such that the open end of each of said radioactive source housings is the closest possible distance to said collimator opening, and said closed position corresponding to rotating said drum 180° from said open position such that the open end of each of said radioactive source housings in the farthest possible distance from said collimator opening;

gamma ray detection means for detecting backscattered gamma rays from a source external to said shielded housing;

processing means for monitoring the number of backscattered gamma rays detected by said detecting means and displaying a count signal detecting means and displaying a count signal representative thereof;

means for detecting any significant change in said count signal as said low energy gamma rays are selectively directed towards adjacent prescribed volumes of said object, the number of backscattered gamma rays noticeably changing if one of said adjacent prescribed volumes contains contraband;

whereby contraband within one of said prescribed volumes may be detected by monitoring changes in said count signal.

2. The portable contraband detection system as set forth in claim 1 wherein said processing means includes alarm means for automatically determining when said count signal exceeds a prescribed threshold.

3. The portable contraband detection system as set forth in claim 2 wherein said prescribed threshold comprises a reference count obtained from holding said collimator opening adjacent a reference volume of said object.

4. The portable contraband detection system as set forth in claim 3 wherein said alarm means is for further generating an audible alarm signal in response to determining that said count signal exceeds said reference count by a prescribed amount.

5. The portable contraband detection system as set forth in claim 2 wherein said means for displaying said count signal includes a visual indicator mounted within a display head electrically coupled to said processing means, said display head being selectively adjustable to enable said displayed count signal to be more readily visible.

6. The portable contraband detection system as set forth in claim 5 wherein said display head is selectively detachable from a housing wherein said processing means, shutter means, and gamma ray generating means are located.

7. The portable contraband detection system as set forth in claim 1 wherein said plurality of radioactive sources received in said drum include a source of americium 241 and a source of barium 133.

8. The portable contraband detection system as set forth in claim 7 wherein said means for selectively rotating said drum is controlled by application of a manual force to a lever coupled to said shaft.

9. The portable contraband detection system as set forth in claim 8 wherein said shutter assembly further includes mechanical biasing means for forcing said drum to rotate to the closed position of said shutter assembly absent the application of said manual force to said lever.

10. The portable contraband detection system as set forth in claim 9 wherein said shutter assembly further includes latch means for selectively locking said drum so that said shutter assembly is locked in its open position.

* * * * *

UNITED STATES PATENT AND TRADEMARK OFFICE
CERTIFICATE OF CORRECTION

PATENT NO. : 5,068,883
DATED : November 26, 1991
INVENTOR(S) : De Haan, et al.

It is certified that error appears in the above-identified patent and that said Letters Patent is hereby corrected as shown below:

IN THE CLAIMS: Claim 1, column 12, lines 6-7, delete "detecting means and displaying a count signal".

Signed and Sealed this

First Day of June, 1993

Attest:

MICHAEL K. KIRK

Attesting Officer     Acting Commissioner of Patents and Trademarks